US00PP08548P

United States Patent [19]

Desclaux et al.

[11] Patent Number: Plant 8,548

[45] Date of Patent: Jan. 18, 1994

[54] STANDARD CARNATION NAME CARICIA

[75] Inventors: Jean L. Desclaux, Paris, France; I. Uto, Salinas, Calif.

[73] Assignee: Laboratorie de Physiologie Vegetale + Establissments Barbaret et Blanc, Paris, France

[21] Appl. No.: 817,431

[22] Filed: Jan. 6, 1992

[51] Int. Cl.[5] ..... A01H 5/00

[52] U.S. Cl. ..... Plt./72.1

[58] Field of Search ..... Plt. 71.1, 72.1, 73.1

*Primary Examiner*—Howard J. Locker

*Attorney, Agent, or Firm*—Tilton, Fallon, Lungmus & Chestnut

[57] ABSTRACT

A new standard carnation cultivar particularly distinguished by the Empire Rose colored flower petals. These flowers are of medium size and are borne singly on long, strong stems and bloom profusely during the recurrent blooming seasons of Spring and Fall. This plant has a vigorous upright growth habit and abundant foliage.

1 Drawing Sheet

BACKGROUND OF THE NEW PLANT

My new carnation cultivar originated as a sport of the variety Lontarion (U.S. Plant Pat. No. 5,435) being grown at LaLonde, Les Maures, France, this particular sport having been discovered and propagated by me with cuttings for testing and evaluation because of its unusual flower coloring. The plant was first asexually reproduced at La Londe Les Maures, France. The cultivar Caricia originated as a naturally occurring whole plant mutation. The initial propagation by cuttings proved to be successful and further propagation confirmed that the new variety retained all of the distinguishing characteristics of the original mutation and that these characteristics hold true from generation to generation and appear to be firmly fixed.

DESCRIPTION OF THE DRAWING

This new carnation cultivar is illustrated by the accompanying photographic drawing which, in full color, shows the distinguishing color characteristics and flower form of this plant, the color rendition being as nearly true as it is reasonably possible to obtain by conventional photographic procedures.

DESCRIPTION OF THE NEW PLANT

The following is a detailed description of our new carnation plant with the color designations according to The R.H.S. Colour Chart of The Royal Horticultural Society of London, England.

THE PLANT

Origin: Sport.

Parentage:

*Sport parent.*—Lontarion (U.S. Plant Pat. No. 5,435).

Classification:

*Botanic.*—Dianthus caryophyllus.

*Commercial.*—Standard carnation.

Form: Erect bush having at least four stems emitted near the ground.

Height: Approximately 79 cm., in average at 8 months.

Cane length: Less than 15 cm. because of pinching.

Branching character: The plant is vigorous and robust, with lots of branching.

Growth: Vigorous, upright and rigid.

Foliage:

*Quantity.*—Abundant.

*Number of leaves.*—More than 120.

Size of leaf.—Approximately 9.2 cm. long and 0.7 cm. wide, in average at the seventh node.

*Leaf shape.*—Oblong shaped with very little pronounced leaf roll, especially at the upper part.

*Texture.*—Leathery.

*Color.*—Upper side — 189-A. Under side — 189-A.

Ribs and veins: Hardly noticeable.

Rachis: Hardly noticeable.

THE BUD

Size:

*Diameter.*—Averages about 2.6 cm.

*Length.*—Averages about 4.2 cm.

Form: Ovoid.

Rate of opening: Normal for carnations.

Color of petals:

*When sepals first divide.*—48-D.

*When petals begin to unfurl.*—Between 48-C and 48-D.

Sepals:

*Number.*—5.

*Shape.*—The sepals are hooded over the bud before dividing and stand up as the flower petals unfurl. The sepals are joined together at the lower part and sharp pointed at the extremity.

*Color.*—Inside — 145-D. Outside — 138-A and 144-C are the colors of the longitudinal stripes of the sepals.

Striae: Longitudinal striae.

Calyx

*Shape.*—Campanulate.

*Size.*—Medium.

*Splitting.*—The calyx very rarely splits.

*Aspect.*—Smooth.

Flower stem:

*Length.*—About 55 cm. in average.

*Character.*—Rigid and erect.

*Color.*—189-A.

THE FLOWER

Blooming habit: Recurrent and profuse during the mid-season of Spring and Fall.

Size of bloom: Medium.

*Diameter.*—About 7.2 cm. in average.

*Depth.*—About 5.2 cm. in average.

Borne: Singly.

Shape:

*When bloom first opens.*—High centered.

*When bloom matures.*—High centered.

Petalage:

*Number of petals.*—Averages about 70.

*Arrangement.*—Imbricated.

*Form.*—Fan-shaped with serrated outer margin.

*Texture.*—Soft.

*Appearance.*—Satiny.

*Color.*—Outer petal — between 48-C and 48-D. Base — Greenish. Reverse side — 48-D. Inside petal — about the same as the outer petals.

*Petaloids.*—Number: 2 to 8. Size: Smaller than petals. Color: The same as petals.

Persistence: The petals hang on and dry.

Fragrance: A light fragrance is perceptible.

Lasting quality:

*As a cut flower.*—At least 10 days with vase keeping.

Disease resistance: Tolerant to *Fusarium oxysporum.* Normal resistance for other diseases.

THE REPRODUCTIVE ORGANS

Stamens:

*Number.*—4 to 11.

*Arrangement.*—Around the ovary.

*Pollen.*—Some is found on the stamens.

*Anthers.*—Size: Less than 4 mm.

*Filaments.*—Length: About 2 cm. in average. Color: Whitish.

Pistils:

*Number.*—2 to 4.

*Styles.*—Length: About 1.5 cm. in average. Color: Pink.

*Stigmas.*—Color: Pink.

Character of the ovaries: The ovary is slightly ribbed.

This new variety most closely resembles Lontarion (U.S. Plant No. 5,435), but is particularly distinguished by the Empire Rose color and shorter stem.

I claim:

1. A new and distinctive carnation cultivar substantially as herein shown and described, characterized by the Empire Rose color of the flower which is borne singly on long, strong stems and which blooms profusely during the recurrent blooming seasons of Spring and Fall.

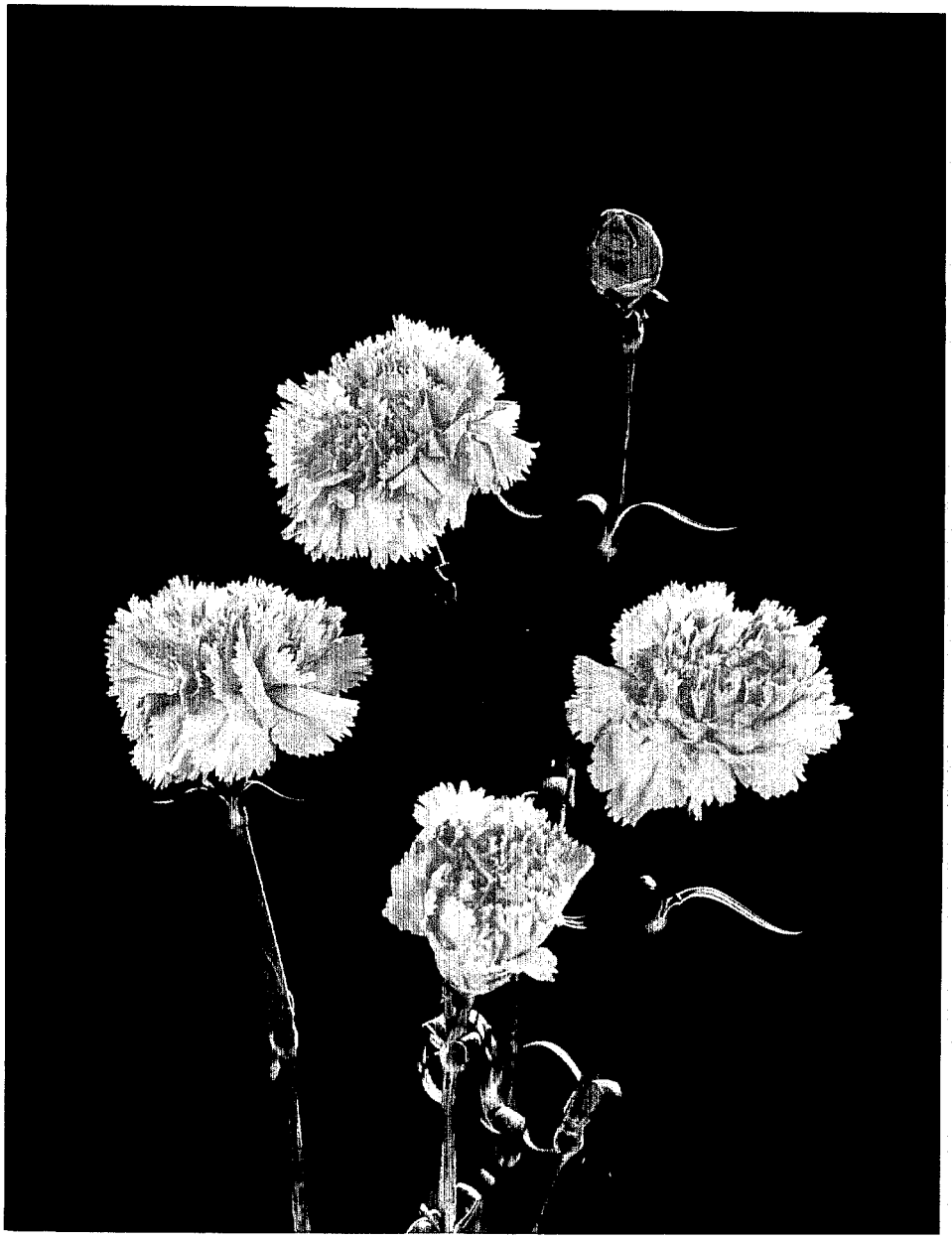

* * * * *